United States Patent
Bugarel et al.

(10) Patent No.: US 10,323,286 B2
(45) Date of Patent: Jun. 18, 2019

(54) SEROTYPE DISCRIMINATION BIOMARKERS TO DISTINGUISH INFANTIS FROM HEIDELBERG AND NEWPORT FROM HADAR

(71) Applicant: Texas Tech University System, Lubbock, TX (US)

(72) Inventors: Marie Bugarel, Lubbock, TX (US); Kendra Nightingale, Lubbock, TX (US); Guy Loneragan, Wolfforth, TX (US); Mindy M. Brashears, Wolfforth, TX (US)

(73) Assignee: Texas Techn University System, Lubbock, TX (US)

( * ) Notice: Subject to any disclaimer, the term of this patent is extended or adjusted under 35 U.S.C. 154(b) by 0 days.

(21) Appl. No.: 15/563,838

(22) PCT Filed: Mar. 30, 2016

(86) PCT No.: PCT/US2016/024990
§ 371 (c)(1),
(2) Date: Oct. 2, 2017

(87) PCT Pub. No.: WO2016/160975
PCT Pub. Date: Oct. 6, 2016

(65) Prior Publication Data
US 2018/0094300 A1    Apr. 5, 2018

Related U.S. Application Data

(60) Provisional application No. 62/140,089, filed on Mar. 30, 2015.

(51) Int. Cl.
| | | |
|---|---|---|
| C12Q 1/68 | (2018.01) | |
| C12Q 1/689 | (2018.01) | |
| C12Q 1/6806 | (2018.01) | |
| C12Q 1/686 | (2018.01) | |

(52) U.S. Cl.
CPC ........... *C12Q 1/689* (2013.01); *C12Q 1/6806* (2013.01); *C12Q 1/686* (2013.01); *C12Q 2600/158* (2013.01); *C12Q 2600/16* (2013.01); *Y02A 50/451* (2018.01)

(58) Field of Classification Search
None
See application file for complete search history.

(56) References Cited

U.S. PATENT DOCUMENTS

| 8,268,984 B2 | 9/2012 | Tourniaire |
| 2009/0298076 A1 | 12/2009 | Tourniaire |
| 2013/0280714 A1 | 10/2013 | Fields et al. |
| 2014/0080130 A1 | 3/2014 | Cummings et al. |

FOREIGN PATENT DOCUMENTS

| WO | 2012145557 A1 | 10/2012 |
| WO | 2015148785 A1 | 10/2015 |

OTHER PUBLICATIONS

GenBank Accession No. CP001120.1, "*Salmonella enterica* subsp. *enterica serovar* Heidelberg str. SL476, complete genome", Jan. 31, 2014.
GenBank Accession No. CP006053.1, "*Salmonella enterica* subsp. *enterica serovar* Bareilly str. CFSAN000189, complete genome", Jul. 16, 2013.
Hong, Yang et al. "Rapid screening of *Salmonella enterica* serovars Enteritidis, Hadar, Heidelberg and Typhimurium using a serologically-correlative allelotyping PCR targeting the O and H antigen alleles" BMC Microbiology, Oct. 9, 2008, 8:178 (8 pages).
International Search Report and Written Opinion [AU/RO] PCT/US2016/024990 dated Jun. 3, 2016.
Liu, B. et al., "PCR identification of *Salmonella* serogroups based on specific targets obtained by comparative genomics", International Journal of Food Microbiology, 2011, vol. 144, pp. 511-518.
Majchrzak, M. et al., "TRS-based PCR as a potential tool for inter-serovar discrimination of *Salmonella enteritidis*, S. Typhimurium, S. Infantis, S. Virchow, S. Hadar, S. Newport and S. Anatum", Molecular Biology Reports, 2014, vol. 41, pp. 7121-7132.
Salem, I. B. et al., "Two five-plex PCRs methods for identification of common *Salmonella* spp. *serotypes*", Annals of Microbiology, 2010, vol. 60, pp. 135-141.

*Primary Examiner* — Jehanne S Sitton
(74) *Attorney, Agent, or Firm* — Edwin S. Flores; Daniel J. Chalker; Chalker Flores, LLP

(57) ABSTRACT

The present invention provides a set of oligonucleotides to screen for the presence of targeted *Salmonella* serotypes in enrichment or to characterize presumptive colonies. The set of oligonucleotides includes at least one set of primers and probe for the detection of *Salmonella* serotype selected from *Newport*, *Heidelberg*, *Infantis*, and *Hadar* and to discriminate between. These new markers can be used after the initial screening assay described herein as a discrimination assay to differentiate *S. Heidelberg* from *S. Infantis* and *S. Hadar* from *S. Newport*.

9 Claims, No Drawings

Specification includes a Sequence Listing.

SEROTYPE DISCRIMINATION BIOMARKERS TO DISTINGUISH INFANTIS FROM HEIDELBERG AND NEWPORT FROM HADAR

TECHNICAL FIELD OF THE INVENTION

The present invention relates generally to methods and compositions used for the detection of bacteria of the genus *Salmonella* and specifically to serotype discrimination biomarkers to distinguish, e.g., *Infantis* from *Heidelberg* and *Newport* from *Hadar*.

BACKGROUND OF THE INVENTION

Without limiting the scope of the invention, its background is described in connection with methods and compositions used for the molecular discrimination of *Salmonella* serotypes. *Salmonella* is a genus of bacteria that may cause severe infections leading to bacterial enteric illness in both humans and animals, e.g., salmonellosis, which include gastro-enteritis, as well as typhoid and para-typhoid fevers. Millions of human cases are reported every year, and the diseases result in thousands of deaths worldwide. In recent years, problems related to *Salmonella* have increased significantly, both in terms of incidence and severity of cases of human salmonellosis.

U.S. Pat. No. 8,268,984, entitled, "Detection of *Salmonella* by Real-Time Multiplex PCR," discloses the detection of *Salmonella* by nucleic acid amplification and provides primer and probe oligonucleotides that can be used in multiplex to detect *Salmonella* in real-time amplification. The oligonucleotides of the invention detect all group I serotypes, and have an increased *Salmonella* detection range and cover seven *Salmonella* groups.

SUMMARY OF THE INVENTION

*Salmonella* is an important cause of human and animal morbidity and mortality. Furthermore, *Salmonella* can be divided into a variety of different serotypes yet the traditional approach to serotyping is expensive, slow, and requires considerable expertise. This is important because several serotypes are regulated as adulterants in laying hen and broiler flocks of *Gallus* chickens in Europe (e.g., S. Enteritidis, S. Typhimurium, *S. Infantis*, S. Virchow, and *S. Hadar*) and some are likely to be targeted for regulation in raw foods in the United States (e.g., S. Typhimurium, *S. Newport*, *S. Heidelberg*, and *S. Hadar*).

In one embodiment, the present invention includes a pair of oligonucleotides for the identification of a *Salmonella* serotype comprising: at least one oligonucleotide pair selected from: a first primer set having SEQ ID NOS: 1 and 3 for the amplification of one or more sequences and a first probe having SEQ ID NO: 2 for discrimination with *S. Infantis* and identification of *S. Heidelberg*; a second primer set having SEQ ID NOS: 4 and 6 for the amplification of one or more sequences and a second probe having SEQ ID NO: 5 for discrimination with *S. Heidelberg* and identification of *S. Infantis*; a third primer set having SEQ ID NOS: 7 and 9 for the amplification of one or more sequences and a third probe having SEQ ID NO: 8 for discrimination with *S. Newport* and identification of *S. Hadar*; or a fourth primer set having SEQ ID NOS: 10 and 12 for the amplification of one or more sequences and a fourth probe having SEQ ID NO: 11 for discrimination with *S. Hadar* and identification of *S. Newport*. In one aspect, the at least one oligonucleotide pair includes the first, second, third and fourth primer sets and the respective first, second, third and fourth probes, for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively. In another aspect, the *Salmonella* serotype is selected from *Newport, Heidelberg, Infantis*, and *Hadar*. In another aspect, the oligonucleotides further comprise at least one detection label. In one aspect, the amplification is a multiplex-, or a real-time multiplex-amplification process.

Another embodiment of the present invention includes a kit for the identification of a *Salmonella* serotype comprising: a pair of oligonucleotide primers comprising SEQ ID NOS: 1 and 3, SEQ ID NOS: 4 and 6, SEQ ID NOS: 7 and 9, or SEQ ID NOS: 10 and 12 for the amplification of one or more sequences of one or more *Salmonella* serotypes; one or more probes selected from SEQ ID NO: 2, SEQ ID NO: 5, SEQ ID NO: 8, and SEQ ID NO: 11 for the identification of one or more *Salmonella* serotypes; reagents for PCR amplification; and instructions for determining the *Salmonella* serotype based on the product of amplification using the primers and probes. In one aspect, the kit further comprises at least one selected from a nucleic acid extraction solution; a DNA polymerase; at least one dNTPs; a buffer having a pH adapted to a polymerase activity; a PCR Master Mix; and an instruction set for performing a real-time multiplex amplification to detect a *Salmonella* serotype. In another aspect, the at least one oligonucleotide pair includes the first, second, third and fourth primer sets and the first, second, third and fourth probes, for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively. In one aspect, the amplification is a multiplex-, or a real-time multiplex-amplification process.

Yet another embodiment of the present invention includes a method of detecting *Salmonella* in a sample comprising the steps of: providing a nucleic acid sample suspected of having one or more *Salmonella* serotypes; adding a pair of primers to the nucleic acid sample, wherein the set of primers comprise at least one primer set selected from SEQ ID NOS: 1 and 3; SEQ ID NOS: 4 and 6; SEQ ID NOS: 7 and 9; and SEQ ID NOS: 10 and 12; contacting the amplified nucleic acid sample with one or more *Salmonella* isolate identification probes selected from SEQ ID NO: 2, SEQ ID NO: 5, SEQ ID NO: 8, and SEQ ID NO: 11; amplifying the nucleic acid sample using the set of primers to form an amplified nucleic acid sample; and detecting the presence of the one or more *Salmonella* isolate identification probes, wherein a positive detection is indicative of at least one *Salmonella* being present in the sample. In one aspect, the amplified nucleic acid sample is a double stranded DNA and the one or more *Salmonella* isolate identification probes are destroyed by a 5' to 3' exonuclease activity of a polymerase thereby releasing the positive detection, wherein the positive detection is a free fluorophore. In another aspect, the method further comprises the step of homogenizing a tissue sample to produce a nucleic acid sample. In another embodiment, the method further comprises the step of extracting the nucleic acids from a homogenized sample. In another aspect, the at least one oligonucleotide pair includes the first, second, third and fourth primer sets and the first, second, third and fourth probes, for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively. In another aspect, the process is a real-time amplification process. In one aspect, the amplification is a multiplex-, or a real-time multiplex-amplification process.

Yet another embodiment of the present invention includes a method of checking the safety of a foodstuff for *Salmonella* comprising the steps of: providing a foodstuff suspected of being contaminated with *Salmonella*; homogenizing the foodstuff; extracting a nucleic acid sample from a homogenized foodstuff; adding a set of primers to the nucleic acid sample, wherein the set of primers comprise at least one primer set selected from SEQ ID NOS: 1 and 3; SEQ ID NOS: 4 and 6; SEQ ID NOS: 7 and 9; and SEQ ID NOS: 10 and 12; adding one or more *Salmonella* isolate identification probes to the nucleic acid sample, wherein the one or more *Salmonella* isolate identification probes are selected from SEQ ID NO: 2, SEQ ID NO: 5, SEQ ID NO: 8, and SEQ ID NO: 11; amplifying the nucleic acid sample using the set of primers to from an amplified nucleic acid sample to form a double stranded DNA; destroying the one or more *Salmonella* isolate identification probes as the double stranded DNA is formed; releasing a fluorophore attached to the one or more *Salmonella* isolate identification probes; and detecting the presence of the fluorophore, wherein a positive detection is indicative of at least one *Salmonella* being present in the sample. In one aspect, the foodstuff is for human consumption, animal consumption or both. In another aspect, the foodstuff is a food or a beverage. In another aspect, the at least one oligonucleotide pair includes the first, second, third and fourth primer sets and the first, second, third and fourth probes, for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively. In one aspect, the amplification is a multiplex-, or a real-time multiplex-amplification process.

Yet another embodiment of the present invention includes a primer-probe set for real-time PCR assays to identify *Salmonella* isolate comprising: at least one oligonucleotide set selected from SEQ ID NOS: 1 and 3, SEQ ID NOS: 4 and 6, SEQ ID NOS: 7 and 9, and SEQ ID NOS: 10 and 12 for the amplification of one or more sequences of one or more *Salmonella* serotype. In one aspect, primer-probe set further comprises one or more probes selected from SEQ ID NO: 2, SEQ ID NO: 5, SEQ ID NO: 8, and SEQ ID NO: 11 for the identification of one or more *Salmonella* isolate. In one aspect, the primers and probes are used in an amplification that is a multiplex-, or a real-time multiplex-amplification process.

Yet another embodiment of the present invention includes a method of checking the safety of a foodstuff for *Salmonella* comprising the steps of: providing a foodstuff suspected of being contaminated with *Salmonella*; homogenizing the foodstuff; extracting a nucleic acid sample from a homogenized foodstuff; determining the presence or absence of one or more of the following: *Salmonella* selected from *Newport*, *Heidelberg*, *Infantis*, and *Hadar* using primers and probes SEQ ID NO: 13 to 24; and identifying further a *Salmonella* serotype comprising: at least one oligonucleotide pair selected from: a first primer set having SEQ ID NOS: 1 and 3 for the amplification of one or more sequences and a first probe having SEQ ID NO: 2 for discrimination with *S. Infantis* and identification of *S. Heidelberg*; a second primer set having SEQ ID NOS: 4 and 6 for the amplification of one or more sequences and a second probe having SEQ ID NO: 5 for discrimination with *S. Heidelberg* and identification of *S. Infantis*; a third primer set having SEQ ID NOS: 7 and 9 for the amplification of one or more sequences and a third probe having SEQ ID NO: 8 for discrimination with *S. Newport* and identification of *S. Hadar*; or a fourth primer set having SEQ ID NOS: 10 and 12 for the amplification of one or more sequences and a fourth probe having SEQ ID NO: 11 for discrimination with *S. Hadar* and identification of *S. Newport*. In one aspect, the amplification is a multiplex-, or a real-time multiplex-amplification process.

DESCRIPTION OF THE DRAWINGS

None.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Various *Salmonella* strains are common foodborne microbes that cause disease in humans and animals. For example, some strains can cause intestinal infections, while others can cause typhoid fever. Because of the large variety of *Salmonella* strains present and the different pathogenic effects of these strains, it is important to develop rapid and flexible assays that have the capacity to distinguish between these strains.

Presently, *Salmonella* serotype determination takes a long period of time and can be inaccurate. This technology allows for the rapid characterization of *Salmonella*, and specifically distinguishes between those serotypes in the United States and European Union, allowing government and industry to make a determination of a serotype within hours that would have previously taken days. For the most part *Salmonella* serotyping has been used to characterize isolates from culture confirmed samples. The present invention provides screening enrichments for the presence (or absence) of regulated (and potentially regulated) *Salmonella* serotypes so that the decision can be made to accept or reject a food product. This benefit is especially important with regard to perishable food products.

The invention provides oligonucleotides that enable the detection of *Salmonella* by nucleic acid hybridization, notably by nucleic acid amplification, more particularly, by PCR, advantageously by multiplex amplification (e.g., multiplex PCR), very advantageously, by real-time multiplex amplification (e.g., real-time multiplex PCR).

The present invention provides a primer-probe based real-time PCR (RTi PCR) assays to identify whether a *Salmonella* isolate (belongs to the regulated serotypes: 1 assay for Europe and 1 assay for the United States) or if it is outside of that group of serotypes. Specifically, unique primers and probes were developed to detect, e.g., genes SNSL254_A0607 (for *Newport* and *Hadar*, Accession number CP001113), SNSL254_A0607 (for *Newport* and *Hadar*, Accession number CP001113), and CFSAN002069_17050 (for *Heidelberg* and *Infantis*, Accession number CP005390), for the 4 out of the 5 regulated serotypes in the European Union. With this approach, the invention can be used to accurately determine the presence of a *Salmonella* isolate belonging to the regulated and/or potentially regulated serotypes selected from *Newport, Heidelberg, Infantis*, and *Hadar*.

The present invention includes a rapid assay to quickly categorize a *Salmonella* isolate in the United States or European Union depending on the gene targets (and identify them as regulated and/or potentially regulated), selected from *Newport, Heidelberg, Infantis*, and *Hadar*. This invention allows key stakeholders (i.e., government and industry) to quickly make decision (within hours) that today would take days to determine which is important for perishable products. The present invention provides an assay that can quickly recognize whether or not a sample contains a regulated (or potentially regulated) *Salmonella* serotype. In addition, the assay could be used for downstream applications to characterize suspect colonies on plates.

Presently *Salmonella* serotype determination takes a long period of time and is invariably inaccurate. The present invention allows for the rapid characterization of *Salmonella* as being regulated or not. Also, if it is regulated, the present invention can be used to further categorize which of the regulated serotypes it is. The present invention includes primers to detect 2 batteries of sequences one specifically for the United States and one for the European Union.

Serotypes were selected to be tested against the markers in the RT PCR assay based on their prevalence in human and non-human cases of salmonellosis, according to data collected by the CDC. In addition to the five targeted serotypes, 30 serotypes with the highest percentages of reported cases of salmonellosis attribution were included. Also included in the exclusivity panel were serotypes that very rarely caused disease, or only caused disease in animals. To investigate the intra-serotype variability, when it was possible, the present inventors selected at least 25 strains for each targeted serotype and 5 strains for each of the 30 most prevalent serotypes. In total, the exclusivity panel includes 121 serotypes from *S. enterica* subsp. *enterica*, together with few strains of the 5 other *Salmonella* subspecies. Also included outside genus isolates from the Enterobacteriaceae family as well as similar organisms to *Salmonella enterica*. These strains belong to 13 different genera. The inclusivity panel included S. Typhimurium (25), S. Enteritidis (26), *S. Newport* (30); 4 of which were characterized as clade A and 5 as clade B, *S. Heidelberg* (27) and *S. Hadar* (25). The exclusivity panel included *Salmonella* strains: S.I 4,5,12:b:- (1), S.I 4,5,12:b:- var. L(+) tartrate (1), S.I 1,4,[5],12:i:- (17), S.I 4,5,12:r:- (1), S.1,4,[5],12:-:1,2 (1), S.I 6,7:-:1,5 (1), S.I 6,7:k:- (1), S.II (2), S.IIIa 18:z4,z23:- (1), S.IIIa (1), S.IIIb 50:k:z (1), S.IIIb 50:r:z (1), S.IIIb 61:1,v:1,5,7 (1), S.IV 44:z4,z23:- (1), S.IV 48:g,z51:-(1), S.IV 50:g,z51:- (1), S.V (1), Aarhus (1), Aberdeen (1), Abony (1), Adelaide (1), Agbeni (1), Agona (5), Alachua (1), Albany (1), Amager (1), Anatum (4), Anatum variant 15+ (1), Apapa (1), Arechaveleta (1), Baildon (1), Bardo (1), Bareilly (5), Barranquilla (1), Berta (1), Blockley (1), Bovismorbificans (1), Braenderup (5), Brandenburg (3), Bredeney (4), Carrau (1), Cerro (5), Chester (1), Choleraesuis (1), Colindale (1), Concord (1), Copenhagen (1), Corvallis (1), Cotham (1), Cubana (1), Derby (3), Dublin (3), Durban (1), Ealing (1), Florida (1), Gaminara (1), Give (3), Give variant 15+ (1), Glostrup (1), Grumpensis (1), Hartford (1), Havana (2), Hindmarsh (1), Holcomb (1), Hvitthingfoss (1), Ibadan (1), Indiana (1), *Infantis* (12), Inverness (1), Istanbul (1), Itami (1), Javiana (5), Johannesburg (1), Kentucky (12), Kiambu (1), Kintambo (1), Kottbus (1), Kuzendorf (1), Lexington (1), Lille (4), Litchfield (1), Liverpool (1), Livingstone (1), London (1), Luciana (1), Madelia (1), Manhattan (2), Mbandaka (6), Meleagridis (5), Miami (1), Mikawasima (1), Minnesota (1), Mississippi (5), Monschaui (1), Montevideo (11), Muenchen (9), Muenster (2), Napoli (1), Norwich (1), Ohio (2), Oranienburg (5), Orion (1), Panama (2), ParatyphiB (5), Pomona (1), Poona (1), Potsdam (1), Putten (1), Reading (11), Richmond (1), Rissen (1), Roodeport (1), Rubislaw (1), SaintPaul (5), SanDiego (1), Saphra (1), Schwarzengrund (5), Senftenberg (5), Stanley (1), Sundsvall (2), Telekelbir (1), Tennessee (1), Thompson (5), Typhi (5), Uganda (2), Urbana (1), Virchow (10), Wandsworth (1), Waycross (1), Weltevreden (1), Worthington (4). The non-*Salmonella* strains included *Aeromonas hydrophila/caviae* (1), *Citrobacter freundii* (1), *Cronobacter sakazakii* (1), *Enterobacter aerogenes* (1), *Hafnia paralvei* (1), *Klebsiella oxytoca* (1), *Klebsiella pneumoniae* (1), *Pantoea agglomerans* (1), *Pseudomonas fluorescens* (1), *Pseudomonas fragi* (1), *Pseudomonas aeruginosa* (1), *Proteus vulgaris* (1), *Serratia marcesans* (1), *Shigella flexneri* (1), *Shigella sonneii* (1), *Vibrio mimicus* (1), *Vibrio parahaemolyticus* (1), *Yersinia entercolitica* (1).

The present invention provided DNA extractions that were either provided or were performed as described herein. In brief, organisms were grown up on a BHI agar plate and one isolated colony was transferred into 50 µl of distilled water. The tubes were incubated for 10 minutes at 95-99° C. and then centrifuged for 3 minutes at maximum speed. The supernatant containing the DNA was then transferred to a fresh 1.5 ml microcentrifuge tube and stored at −20° C. until use. DNA extractions provided by ANSES were performed using the Instagene Matrix (BioRad, Berkeley, Calif., USA) following the manufacturer's recommendations. The PureLink Genomic DNA Mini Kit (Invitrogen, Carlsbad, Calif., USA) was used to extract the genomic DNA following the manufacturer's recommendations, and it was then quantified using the Nanodrop 2000c Spectrophotometer (ThermoScientific, Waltham, Mass., USA).

The present invention provided RNA extractions from an overnight culture of each of the 5 serotypes of interest. Cultures were grown in 50 mL flasks with an estimated final concentration of roughly $10^9$ CFU/ml. The cultures were pelletized and treated with RNA Protect (Qiagen, Venlo, The Netherlands) for overnight storage. Extraction was performed using a modified version of the TRI Reagent protocol (Molecular Research Center, Inc., Cincinnati, Ohio). Briefly, pelleted cells were resuspended in TRI Reagent to lyse, and then bromochloropropane (BCP) was added to induce phase separation. A supernatant containing RNA was transferred to a new tube, then isopropanol was added to precipitate the RNA, the tubes were spun to pelletize the RNA, and then this supernatant was removed. The pellets were washed with an Ethanol solution, dried, treated with DNAse (Promega, Madison, Wis.), quantified using the Nanodrop 2000c Spectrophotometer (ThermoScientific, Waltham, Mass., USA), and stored in −80° C. until ready for use in quantitative reverse transcriptase (qRT) realtime (RTi) PCR. The Black Hole Quencher Dye-2 (BHQ-2™) (Sigma-Aldrich), and HEX™ dye (Life Technologies) were used as instructed for inclusion in an oligonucleotide, e.g., as a HEX™ dye or BHQ-2 Phosphoramidite.

The present inventors have previously identified molecular markers to specifically detect the four important serotypes of *Salmonella: Newport, Heidelberg, Infantis*, and *Hadar*. However, only the serotypes Typhimurium and Enteritidis are specifically identified using their respective markers, STM2 and Ent6. The marker Heid2 detects both *S. Heidelberg* and *S. Infantis* strains. In addition, the marker Newp2 detects both *S. Newport* and *S. Hadar*. In order to clarify the identity of the detected strains with Heid2 and Newp2 markers, the present inventors developed a new set of 4 markers that allow the discrimination between the related serotypes with the previous set of markers.

TABLE 1

Table of oligonucleotides and sequence (F - Forward Primer, R - Reverse Primer, P - Probe).

| Primer ID | Sequence (5' . . . 3') | Comment |
|---|---|---|
| Heidspe-F3 | TCATGATTATGCCGAAATTATGCG (SEQ ID NO.: 1) | Discrimination with S. Infantis and identification of S. Heidelberg |
| Heidspe-P3 | HEX-AATGGTGGTTGGGATTGGGATAGGTCTC-BHQ2 (SEQ ID NO.: 2) | |
| Heidspe-R3 | ATCATAAGAGACTAATTGCCCATC (SEQ ID NO.: 3) | |
| Infspe-F2 | AAGTTGCCCCCTTGAGTTCC (SEQ ID NO.: 4) | Discrimination with S. Heidelberg and identification of S. Infantis |
| Infspe-P2 | FAM-TGTTGCCAGCGGCATGAAGAAAATCCC-BHQ1 (SEQ ID NO.: 5) | |
| Infspe-R2 | AATGTGCGCACGTTTGGTGG (SEQ ID NO.: 6) | |
| Hadspe-F1 | GAATCAAACCGCTTTATGGTGC (SEQ ID NO.: 7) | Discrimination with S. Newport and identification of S. Hadar |
| Hadspe-P1 | FAM-ATCCGGCGCTGCATGGGTATATGACC-BHQ1 (SEQ ID NO.: 8) | |
| Hadspe-R1 | TGCTCTTGAGCATCCCGTTG (SEQ ID NO.: 9) | |
| Newpspe-F1 | TGATGCTTTCTTATTATGAACAAGG (SEQ ID NO.: 10) | Discrimination with S. Hadar and identification of S. Newport |
| Newpspe-P1 | HEX-ATTATTCTGAGCTAACGCCATCGCAGAGG-BHQ2 (SEQ ID NO.: 11) | |
| Newpspe-R1 | TCTATAGGCATATGAATACTCGC (SEQ ID NO.: 12) | |

TABLE 2

Each marker has been evaluated on a set of DNA extractions of strains belonging to the targeted serotype (inclusivity) and of the non-targeted serotype (exclusivity). Furthermore, the expression of the targeted region was investigated for each marker.

| Marker ID | Inclusivity | Exclusivity | Expression |
|---|---|---|---|
| Heidspe3 | Heidelberg: Detection of 23/23 | Infantis: Detection of 0/11 | Yes |
| Infspe2 | Infantis: Detection of 11/11 | Heidelberg: Detection of 0/23 | Yes |
| Hadspe1 | Hadar: Detection of 22/22 | Newport: Detection of 0/28 | No |
| Newspe1 | Newport: Detection of 28/28 | Hadar: Detection of 0/22 | No |

TABLE 3

Discrimination between serotypes.

| ID | Serotype | Infspe2 | Heidspe3 | Newspe1 | Hadspe1 | Heid2 |
|---|---|---|---|---|---|---|
| | Expression investigation from samples growth into BHI at 37 C. | really low level of expression | expressed | not expressed | not expressed | |
| R1-023 | Newport (T+) | | | 1 | 0 | |
| R1-024 | Newport | | | 1 | 0 | |
| R1-025 | Newport | | | 1 | 0 | |
| R1-026 | Newport | | | 1 | 0 | |
| R1-027 | Newport | | | 1 | 0 | |
| R1-028 | Newport | | | 1 | * | |
| R1-029 | Newport | | | 1 | 0 | |
| R1-030 | Newport | | | 1 | 0 | |
| R1-031 | Newport | | | 1 | 0 | |
| R1-032 | Newport | | | 1 | 0 | |
| R1-033 | Newport | | | 1 | 0 | |
| R1-034 | Newport | | | 1 | 0 | |
| R1-035 | Newport | | | 1 | 0 | |
| R1-036 | Newport | | | 1 | 0 | |
| R1-037 | Newport | | | 1 | 0 | |
| R1-038 | Newport | | | 1 | 0 | |
| R1-039 | Newport | | | 1 | 0 | |
| R1-041 | Newport | | | 1 | 0 | |
| R1-042 | Newport | | | 1 | 0 | |
| T1-470 | Newport | | | 1 | 0 | |
| T1-471 | Newport | | | 1 | 0 | |
| T1-472 | Newport | | | 1 | 0 | |
| T1-473 | Newport | | | 1 | 0 | |

TABLE 3-continued

Discrimination between serotypes.

| ID | Serotype | Infspe2 | Heidspe3 | Newspe1 | Hadspe1 | Heid2 |
|---|---|---|---|---|---|---|
| T1-474 | Newport | | | 1 | 0 | |
| T1-475 | Newport | | | 1 | 0 | |
| T1-476 | Newport | | | 1 | 0 | |
| T1-477 | Newport | | | 1 | 0 | |
| T1-478 | Newport | | | 1 | 0 | |
| T1-248 | Hadar (not detected with 1st screening) | | | 0 | * | |
| T1-391 | Hadar (not detected with 1st screening) | | | 0 | 0 | |
| T1-213 | Hadar (T+) | | | 0 | 1 | |
| T1-231 | Hadar | | | 0 | 1 | |
| T1-235 | Hadar | | | 0 | 1 | |
| T1-267 | Hadar | | | 0 | 1 | |
| T1-289 | Hadar | | | 0 | 1 | |
| T1-314 | Hadar | | | 0 | 1 | |
| T1-332 | Hadar | | | 0 | 1 | |
| T1-357 | Hadar | | | 0 | 1 | |
| T1-358 | Hadar | | | 0 | 1 | |
| T1-359 | Hadar | | | 0 | 1 | |
| T1-361 | Hadar | | | 0 | 1 | |
| T1-362 | Hadar | | | 0 | 1 | |
| T1-363 | Hadar | | | 0 | 1 | |
| T1-364 | Hadar | | | 0 | 1 | |
| T1-366 | Hadar | | | 0 | 1 | |
| T1-373 | Hadar | | | 0 | 1 | |
| T1-374 | Hadar | | | 0 | 1 | |
| T1-378 | Hadar | | | 0 | 1 | |
| T1-379 | Hadar | | | 0 | 1 | |
| T1-382 | Hadar | | | 0 | 1 | |
| T1-387 | Hadar | | | 0 | 1 | |
| T1-391 | Hadar | | | 0 | 1 | |
| 12TT | Infantis (T+) | 1 | 0 | | | |
| 21TT | Infantis | 1 | 0 | | | |
| 26TT | Infantis | 1 | 0 | | | |
| 281TT | Infantis | 1 | 0 | | | |
| 282TT | Infantis | 1 | 0 | | | |
| 284TT | Infantis | 1 | 0 | | | |
| 294TT | Infantis | 1 | 0 | | | |
| 29TT | Infantis | 1 | 0 | | | |
| 307TT | Infantis | 1 | 0 | | | |
| 40TT | Infantis | 1 | 0 | | | |
| C-043 | Infantis | 1 | 0 | | | |
| T1-480 | Heidelberg (T+) | 0 | 1 | | | |
| T1-481 | Heidelberg | 0 | 1 | | | |
| T1-482 | Heidelberg | 0 | 1 | | | |
| T1-483 | Heidelberg | * | 1 | | | |
| T1-484 | Heidelberg | * | 1 | | | |
| T1-485 | Heidelberg | * | 1 | | | |
| T1-486 | Heidelberg | * | 1 | | | |
| T1-487 | Heidelberg (not detected with 1st screening) | * | 0 | | | |
| T1-488 | Heidelberg | * | 1 | | | |
| T1-489 | Heidelberg | * | 1 | | | |
| T1-490 | Heidelberg | * | 1 | | | |
| T1-491 | Heidelberg | * | 1 | | | |
| T1-492 | Heidelberg | * | 1 | | | |
| T1-510 | Heidelberg | 0 | 1 | | | |
| T1-511 | Heidelberg | * | 1 | | | |
| T1-512 | Heidelberg | * | 1 | | | |
| T1-513 | Heidelberg | * | 1 | | | |
| T1-514 | Heidelberg | * | 1 | | | |
| T1-515 | Heidelberg | 0 | 1 | | | |
| T1-516 | Heidelberg | * | 1 | | | |
| T1-518 | Heidelberg | * | 1 | | | |
| T1-519 | Heidelberg | * | 1 | | | |
| T1-520 | Heidelberg | * | 1 | | | |
| T1-521 | Heidelberg | * | 1 | | | |
| T1-522 | Heidelberg | * | 1 | | | |
| T1-293 | Aarhus | * | | | | 0 |
| T1-273 | Aberdeen | 0 | | | | 0 |
| T1-456 | Abony | 0 | | | | 0 |

TABLE 3-continued

Discrimination between serotypes.

| ID | Serotype | Infspe2 | Heidspe3 | Newspe1 | Hadspe1 | Heid2 |
|---|---|---|---|---|---|---|
| T1-204 | Agona | 0 | | | | 0 |
| T1-340 | Amager | 0 | | | | 0 |
| C-001 | Anatum | 0 | | | | 0 |
| T1-421 | Apapa | * | | | | 0 |
| T1-458 | Arechavaleta | 0 | | | | 0 |
| T1-263 | Baildon | 0 | | | | 0 |
| T1-228 | Bareilly | 1 | | | | 0 |
| T1-316 | Barranquilla | * | | | | 0 |
| T1-216 | Berta | 0 | | | | 0 |
| T1-347 | Braenderup | 1 | | | | 0 |
| 1838 | Brandenburg | * | | | | 0 |
| 25RV | Cerro | 0 | | | | 0 |
| T1-448 | Cholerasuis | 1 | | | | 0 |
| T1-439 | Colindale | 1 | | | | 0 |
| T1-304 | Concord | 1 | | | | 0 |
| T1-202 | Copenhagen | 0 | | | | 0 |
| T1-310 | Cotham | 0 | | | | 0 |
| T1-281 | Dublin | 0 | | | | 0 |
| T1-405 | Durban | 0 | | | | 0 |
| C2-060 | Enteritidis | 0 | | | | 0 |
| T1-452 | Florida | 0 | | | | 0 |
| T1-210 | Gaminara | 0 | | | | 0 |
| 1833 | Give | 0 | | | | 0 |
| T1-355 | Glostrup | 0 | | | | 0 |
| T1-213 | Hadar | 0 | | | | 0 |
| T1-377 | Hindmarsh | 0 | | | | 0 |
| T1-224 | Holcomb | 0 | | | | 0 |
| T1-388 | Inverness | 0 | | | | 0 |
| T1-432 | Istanbul | 0 | | | | 0 |
| T1-211 | Javiana | 0 | | | | 0 |
| 1780 | Kentucky | 0 | | | | 0 |
| T1-455 | Kintambo | 0 | | | | 1 |
| T1-375 | Lexington | 0 | | | | 0 |
| 14TT | Lille | * | | | | 0 |
| T1-440 | Liverpool | 0 | | | | 0 |
| T1-392 | Livingstone | 1 | | | | 0 |
| T1-381 | Luciana | 0 | | | | 0 |
| 75TT | Manhattan | 0 | | | | 0 |
| 1811 | Mbandaka | * | | | | 0 |
| 471 | Meleagridis | 0 | | | | 0 |
| T1-265 | Mikawasima | 1 | | | | 0 |
| T1-218 | Mississippi | 0 | | | | 0 |
| 272 | Montevideo | 1 | | | | 0 |
| 1011TT | Muenchen | 0 | | | | 0 |
| T1-470 | Newport-A | 0 | | | | 0 |
| T1-474 | Newport-B | 1 | | | | 0 |
| T1-422 | Norwich | 0 | | | | 0 |
| 1890 | Ohio | * | | | | 0 |
| T1-275 | Oranienburg | 1 | | | | 0 |
| 1853 | Panama | 0 | | | | 0 |
| T1-321 | ParatyphiB | * | | | | 0 |
| T1-271 | Pomona | 0 | | | | 0 |
| T1-214 | Putten | 0 | | | | 0 |
| 680 | Reading | 0 | | | | 0 |
| T1-215 | Richmond | 0 | | | | 0 |
| T1-424 | Roodeport | 0 | | | | 0 |
| T1-396 | S.I 1,4,[5],12:-:1,2 | * | | | | 0 |
| R1-142 | S.I 1,4,[5],12:i:- | 0 | | | | 0 |
| T1-429 | S.I 1,4,5,12:b:- var. L(+) tartrate+ | 0 | | | | 0 |
| T1-354 | S.I 4,5,12:b:- | * | | | | 0 |
| T1-416 | S.I 4,5,12:r:- | 0 | | | | 1 |
| T1-259 | S.I 6,7:-:1,5 | 1 | | | | 0 |
| T1-370 | S.I 6,7:k:- | 1 | | | | 0 |
| T1-305 | S.II salamae | * | | | | 0 |
| T1-401 | S.IIIb 50:k:z | 0 | | | | 0 |
| T1-451 | S.IIIb 50:r:z | 0 | | | | 0 |
| T1-436 | S.IIIb 61:l,v:1,5,7 | 0 | | | | 0 |
| T1-390 | S.IV 44:z4,z23:- (a4,a23) | 0 | | | | 0 |

TABLE 3-continued

Discrimination between serotypes.

| ID | Serotype | Infspe2 | Heidspe3 | Newspe1 | Hadspe1 | Heid2 |
|---|---|---|---|---|---|---|
| T1-272 | S.IV 48:g,z51:- | 0 | | | | 0 |
| T1-446 | S.IV 50:g,z51:- | 1 | | | | 0 |
| T1-209 | S.V | * | | | | 0 |
| T1-246 | SaintPaul | 0 | | | | 0 |
| T1-450 | Saphra | 0 | | | | 0 |
| T1-203 | Schwarzengrund | 0 | | | | 0 |
| T1-208 | Senftenberg | 0 | | | | 0 |
| T1-441 | Sundsvall | 1 | | | | 0 |
| T1-319 | Telekelbir | * | | | | 0 |
| T1-221 | Thompson | 1 | | | | 0 |
| T1-317 | Typhi | 0 | | | | 0 |
| R1-089 | Typhimurium | 0 | | | | 0 |
| 1842 | Uganda | * | | | | 0 |
| T1-447 | Virchow | * | | | | * |
| T1-212 | Wandsworth | 0 | | | | 0 |
| T1-404 | Waycross | 0 | | | | 0 |
| T1-302 | Worthington | 0 | | | | 0 |

Raw data, * means delayed signal (above 32 cycle for the Ct)

invention also include those listed in Table 4. These primers can be used prior to the screen of the present invention to determine *Salmonella* serotypes selected from *S. Newport*, *S. Heidelberg* and *S. Hadar* depending on the primer set and the corresponding probe. As such, the present invention also includes the method of determining which of the following *Salmonella* serotypes are present in a sample selected from *S. Newport, S. Heidelberg, S. Infantis,* and *S. Hadar*.

however, did not amplify with the *Heidelberg* marker (Heid2), and is likely to have been mis-serotyped.

The *Heidelberg* marker (Heid2) detected all the other *S. Heidelberg* isolates tested, but also amplified all 12 of the *S. Infantis* strains that were tested against this marker. This marker detects also one S. Kintambo strain and one S.I 4,5,12:r:- strain. Together these 3 cross-reacting serotypes represent less than 2% of human and non-human cases in the

TABLE 4

The primer and probe sequences are shown in the table below:

| Name | Sequence (5' . . . 3') | |
|---|---|---|
| Ent6 Forward Primer (FPrimer) | TCGTACCTGCTGATGCTGGG | SEQ ID NO: 13 |
| Ent6 Probe | HEX-TATGCGCTGGTTCCGTTCCGTTTTCTGG-BHQ2 | SEQ ID NO: 14 |
| Ent6 Reverse Primer (RPrimer) | AGGATGAAGACGGGTAATGTCC | SEQ ID NO: 15 |
| Newp2 FPrimer | AATGGCTGGTAGCCTGTTCG | SEQ ID NO: 16 |
| Newp2 Probe | Cy5-TCATGCTATGCACTGGGAACAATTTCTGGC-IowaBRQ | SEQ ID NO: 17 |
| Newp2 RPrimer | AGGGAAAGCAAGGAACAGTAG | SEQ ID NO: 18 |
| STM2 FPrimer | AGATATTCCGTAGCAATTGAGTTG | SEQ ID NO: 19 |
| STM2 Probe | FAM-TGTGTTCAAGCAATGGTGAACAAACATAATCCC-BHQ2 | SEQ ID NO: 20 |
| STM2 RPrimer | AATAGCTAAAAATGACTGGGACTC | SEQ ID NO: 21 |
| Heid2 FPrimer | CCTGCAGAAAGATATGTTTGGC | SEQ ID NO: 22 |
| Heid2 Probe | HEX-TTAATCTGTGCGACGAATTGGGCAGCC-BHQ2 | SEQ ID NO: 23 |
| Heid2 RPrimer | TGCGATGAAGATTGATGATGCC | SEQ ID NO: 24 |

Using the primers hereinabove, it was previously found by the present inventors that S. Typhimurium marker (STM2) detects 100% of S. Typhimurium and its somatic and flagellar variant (1,4,[5],12:i:-, 1,4,[5],12:-:1,2 and S. Copenhagen) strains tested, as well as one strain that had been serotyped as *Heidelberg*. This strain of *S. Heidelberg,*

United States between 1999 and 2009 (National *Salmonella* Surveillance Annual Summary 2009).

The *Newport* marker (Newp2) detected all *S. Newport* strains tested, including isolates from both clades A and B, as well as 23 of 25 *S. Hadar* strains that were tested in the study. Furthermore, this marker also detects few strains belonging to other serotypes, such as Bardo, Blockley, Bovismorbificans, Glostrup, Istanbul, Kottbus, Litchfield, Manhattan, Muenchen, and Virchow.

The Enteritidis marker (Ent6) detects 24 out of the 26 S. Enteritidis strains tested. This marker does not strongly cross-react with non-targeted serotypes, but present several weak cross-reactions with diverse serotypes.

Furthermore, the inventors investigated the expression of these 4 targeted regions. The inventors were able to highlight the expression of the targeted regions for S. Typhimurium, *S. Heidelberg* and *S. Newport* markers. Only the Enteritidis marker seems to be located on a non-coding region.

only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "con-

| Marker | Targeted serotypes | Inclusivity panel | Cross-reacted serotypes | % cross-reactivity [a] | Diagnostic sensitivity [b] | Diagnostic specificity [c] |
|---|---|---|---|---|---|---|
| STM2 | *Typhimurium* and its variants | 44/44 | / | 0% | 1 | 1 |
| Ent6 | Enteritidis | 24/26 | / | 0% | 0.96 | 1 |
| Heid2 | Heidelberg | 26/27 | Infantis, Kintambo, S.I 4,5,12:r:- | 1.526% | 0.96 | 0.97 |
| Newp2 | Newport and Hadar | 53/55 | Bardo, Blockley, Glostrup, *Bovismorbificans*, Istanbul, Kottbus, Litchfield, Muenchen, Manhattan, Virchow | 3.582% | 0.96 | 0.97 |

[a] in human cases in the US between 1999 and 2009 according to the CDC report titled National *Salmonella* Surveillance Annual Summary 2009. Only the strong cross-reactions with a Ct < 32 were considered.
[b] Diagnostic sensitivity: number of true positive/number of expected positive (Saah and Hoover, 1997).
[c] Diagnostic specificity: number of true negative/number of expected negative (Saah and Hoover, 1997).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to tain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A kit for the identification of a *Salmonella* serotype comprising:

at least three oligonucleotides selected from:
- a first primer set having SEQ ID NOS: 1 and 3, for the amplification of one or more sequences, and a first probe having SEQ ID NO: 2 attached to a dye, for discrimination with *S. Infantis* and identification of *S. Heidelberg*;
- a second primer set having SEQ ID NOS: 4 and 6, for the amplification of one or more sequences, and a second probe having SEQ ID NO: 5 attached to a dye, for discrimination with *S. Heidelberg* and identification of *S. Infantis*;
- a third primer set having SEQ ID NOS: 7 and 9, for the amplification of one or more sequences, and a third probe having SEQ ID NO: 8 attached to a dye, for discrimination with *S. Newport* and identification of *S. Hadar*; or
- a fourth primer set having SEQ ID NOS: 10 and 12, for the amplification of one or more sequences, and a fourth probe having SEQ ID NO: 11 attached to a dye, for discrimination with *S. Hadar* and identification of *S. Newport*; and at least one selected from a nucleic acid extraction solution; a recombinant DNA polymerase; at least one dNTPs; a buffer having a pH adapted to a DNA polymerase activity; a PCR Master Mix; and an instruction set for performing a real-time multiplex amplification to detect a *Salmonella* serotype.

2. The oligonucleotides of claim 1, wherein the oligonucleotides include the first, second, third and fourth primer sets and the first, second, third and fourth probes, for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively.

3. The oligonucleotides of claim 1, wherein the *Salmonella* serotype is selected from *Newport, Heidelberg, Infantis,* and *Hadar.*

4. A kit for the identification of a *Salmonella* serotype comprising:

a pair of oligonucleotide primers comprising SEQ ID NOS: 1 and 3, SEQ ID NOS: 4 and 6, SEQ ID NOS: 7 and 9, or SEQ ID NOS: 10 and 12 for the amplification of one or more sequences of one or more *Salmonella* serotypes;

one or more probes selected from SEQ ID NO: 2, SEQ ID NO: 5, SEQ ID NO: 8, and SEQ ID NO: 11, wherein each probe is attached to a dye, for the identification of one or more *Salmonella* serotypes; and one or more vials comprising reagents for PCR amplification, including at least one selected from a nucleic acid extraction solution; a DNA polymerase; at least one dNTPs; a buffer having a pH adapted to a polymerase activity; a PCR Master Mix; and instructions for determining the *Salmonella* serotype based on the product of amplification using the primers and probes.

5. The kit of claim 4, further comprising an instruction set for performing a multiplex amplification to detect a *Salmonella* serotype.

6. The kit of claim 5, wherein the instructions provide for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively.

7. The kit of claim 1, wherein the instructions provide for discrimination with *S. Infantis* and identification of *S. Heidelberg*; discrimination with *S. Heidelberg* and identification of *S. Infantis*; discrimination with *S. Newport* and identification of *S. Hadar*; or discrimination with *S. Hadar* and identification of *S. Newport*, respectively.

8. The kit of claim 1, wherein the dye is a fluorescent dye.

9. The kit of claim 4, wherein the dye is a fluorescent dye.

* * * * *

SEQUENCE LISTING

<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
tcatgattat gccgaaatta tgcg                                          24

<210> SEQ ID NO 2
<211> LENGTH: 28
<212> TYPE: DNA
<213> ORGANISM: Artificial Sequence
<220> FEATURE:
<223> OTHER INFORMATION: Synthetic primer

<400> SEQUENCE: 2
aatggtggtt gggattggga taggtctc                                      28

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
atcataagag actaattgcc catc                                          24

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
aagttgcccc cttgagttcc                                               20

<210> SEQ ID NO 5
<211> LENGTH: 27
<212> TYPE: DNA
<213> ORGANISM: Artificial Sequence
<220> FEATURE:
<223> OTHER INFORMATION: Synthetic primer

<400> SEQUENCE: 5
tgttgccagc ggcatgaaga aaatccc                                       27

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
aatgtgcgca cgtttggtgg                                               20

<210> SEQ ID NO 7
<211> LENGTH: 22
<212> TYPE: DNA
<213> ORGANISM: Artificial Sequence

```
<220> FEATURE:
<223> OTHER INFORMATION: Synthetic primer

<400> SEQUENCE: 7
gaatcaaacc gctttatggt gc                                          22

<210> SEQ ID NO 8
<211> LENGTH: 26
<212> TYPE: DNA
<213> ORGANISM: Artificial Sequence
<220> FEATURE:
<223> OTHER INFORMATION: Synthetic primer

<400> SEQUENCE: 8
atccggcgct gcatgggtat atgacc                                      26

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
tgctcttgag catcccgttg                                             20

<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10
tgatgctttc ttattatgaa caagg                                       25

<210> SEQ ID NO 11
<211> LENGTH: 29
<212> TYPE: DNA
<213> ORGANISM: Artificial Sequence
<220> FEATURE:
<223> OTHER INFORMATION: Synthetic primer

<400> SEQUENCE: 11
attattctga gctaacgcca tcgcagagg                                   29

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
tctataggca tatgaatact cgc                                         23

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tcgtacctgc tgatgctggg                                             20
```

<210> SEQ ID NO 14
<211> LENGTH: 28
<212> TYPE: DNA
<213> ORGANISM: Artificial Sequence
<220> FEATURE:
<223> OTHER INFORMATION: Synthetic primer

<400> SEQUENCE: 14
tatgcgctgg ttccgttccg ttttctgg                                    28

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
aggatgaaga cgggtaatgt cc                                          22

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
aatggctggt agcctgttcg                                             20

<210> SEQ ID NO 17
<211> LENGTH: 30
<212> TYPE: DNA
<213> ORGANISM: Artificial Sequence
<220> FEATURE:
<223> OTHER INFORMATION: Synthetic primer

<400> SEQUENCE: 17
tcatgctatg cactgggaac aatttctggc                                  30

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
agggaaagca aggaacagta g                                           21

<210> SEQ ID NO 19
<211> LENGTH: 24
<212> TYPE: DNA
<213> ORGANISM: Artificial Sequence
<220> FEATURE:
<223> OTHER INFORMATION: Synthetic primer

<400> SEQUENCE: 19
agatattccg tagcaattga gttg                                        24

<210> SEQ ID NO 20
<211> LENGTH: 33
<212> TYPE: DNA
<213> ORGANISM: Artificial Sequence
<220> FEATURE:
<223> OTHER INFORMATION: Synthetic primer

```
<400> SEQUENCE: 20
tgtgttcaag caatggtgaa caaacataat ccc                               33

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
aatagctaaa aatgactggg actc                                         24

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
cctgcagaaa gatatgtttg gc                                           22

<210> SEQ ID NO 23
<211> LENGTH: 27
<212> TYPE: DNA
<213> ORGANISM: Artificial Sequence
<220> FEATURE:
<223> OTHER INFORMATION: Synthetic primer

<400> SEQUENCE: 23
ttaatctgtg cgacgaattg ggcagcc                                      27

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tgcgatgaag attgatgatg cc                                           22
```